United States Patent [19]

Fujii et al.

[11] Patent Number: 4,492,792
[45] Date of Patent: Jan. 8, 1985

[54] PROCESS FOR PREPARING 4-AMINO-5-DIALKOXY-METHYLPYRIMIDINE DERIVATIVES

[75] Inventors: Kozo Fujii; Keigo Nishihira; Hiroyuki Sawada; Shuji Tanaka; Mamoru Nakai; Hiroshi Yoshida; Teruhiko Inoue, all of Ube, Japan

[73] Assignee: Ube Industries, Ltd., Ube, Japan

[21] Appl. No.: 461,191

[22] Filed: Jan. 26, 1983

[30] Foreign Application Priority Data

Feb. 4, 1982 [JP] Japan .................. 57-15503
Sep. 10, 1982 [JP] Japan .................. 57-156687

[51] Int. Cl.³ .................................. C07D 239/02
[52] U.S. Cl. ........................................ 544/326
[58] Field of Search ............................. 544/326

[56] References Cited

U.S. PATENT DOCUMENTS

| | | | |
|---|---|---|---|
| 2,602,794 | 7/1952 | Hitchings | 544/326 |
| 3,036,075 | 5/1962 | Kaiser | 544/326 |
| 3,956,327 | 5/1976 | Cresswell | 544/326 |
| 4,039,543 | 8/1977 | Kompis | 544/122 |

FOREIGN PATENT DOCUMENTS

| | | | |
|---|---|---|---|
| 31458 | 10/1970 | Japan | 544/326 |
| 496738 | 12/1937 | United Kingdom | 544/326 |

OTHER PUBLICATIONS

Bredereck, Chem. Ber. 106, 3743 (1973).

*Primary Examiner*—Paul M. Coughlan, Jr.
*Assistant Examiner*—Cecilia Shen
*Attorney, Agent, or Firm*—Frishauf, Holtz, Goodman & Woodward

[57] ABSTRACT

A process for preparing a 4-amino-5-dialkoxymethyl-pyrimidine derivative of the formula:

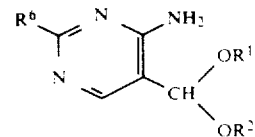

which comprises reacting a propanenitrile derivative represented by the formula (I) or the novel compound represented by formula (II):

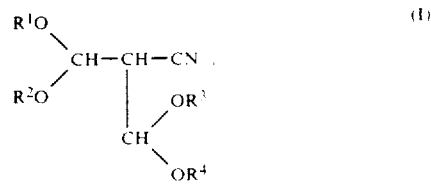

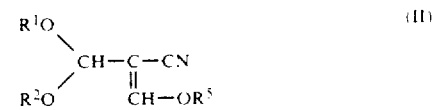

with an amidine of the formula:

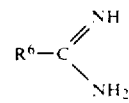

wherein $R^1$ to $R^6$ are as defined in the specification. Also disclosed is a process for making the novel compounds of formula (II).

18 Claims, No Drawings

PROCESS FOR PREPARING 4-AMINO-5-DIALKOXY-METHYLPYRIMIDINE DERIVATIVES

This invention relates to a novel process for preparing a 4-amino-5-dialkoxymethylpyrimidine derivative.

The 4-amino-5-dialoxymethylpyrimidine derivative is utilized as an intermediate for the synthesis of Vitamin-B₁ and its analogues.

Conventionally, as a method for the preparation of a 4-amino-5-dialkoxymethylpyrimidine derivative, the following method has been disclosed in Chem. Ber. 106, 3743 (1973).

First, a 4,6-dichloro-5-formylpyrimidine is reacted with ammonia. Then, the so obtained 4-amino-5-formyl-6-chloropyrimidine is reacted with hydrogen to derive a 4-amino-5-formylpyrimidine, which is subsequently reacted with a trialkoxymethane to prepare the desired 4-amino-5-dialkoxymethylpyrimidine. This method has industrial problems in that the reaction steps are many in number and complicated and that the synthesis of the starting pyrimidine derivative is not easy.

The present inventors have made earnest studies to establish a process by which the 4-amino-5-dialkoxymethylpyrimidine derivative can advantageously be prepared industrially.

As the result, the present inventors found that, when a propanenitrile derivative represented by the general formula (I) or (II)

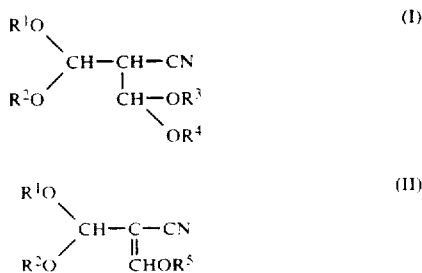

wherein $R^1$, $R^2$, $R^3$, $R^4$ and $R^5$ may be the same or different and each represent a lower-alkyl group; or $R^1$, $R^2$, $R^3$ and $R^4$ may be lower-alkylene groups which are bonded to each other to form a ring or rings, is reacted with an amidine represented by the general formula (III)

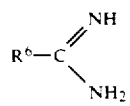

wherein $R^6$ represents a hydrogen atom, a lower-alkyl group or a phenyl group of which the hydrogen atom or atoms may be replaced by a lower-alkyl group, a lower-alkoxy group or a halogen atom, a 4-amino-5-dialkoxymethylpyrimidine derivative represented by the general formula (IV)

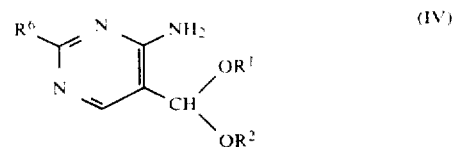

wherein $R^1$, $R^2$ and $R^6$ have the same meanings as defined above, can be prepared with extreme industrial advantage, and accomplished this invention.

As the $R^1$, $R^2$, $R^3$, $R^4$ and $R^5$ in the 2-dialkoxymethyl-3,3-dialkoxypropanenitrile of the above general formula (I) and the 2-alkoxymethylene-3,3-dialkoxypropanenitrile of the above general formula (II) which are starting material of this invention, and in the 4-amino-5-dialkoxymethylpyrimidine derivatives of the above general formula (IV), there may be mentioned a lower-alkyl group such as methyl, ethyl, propyl and butyl.

Alternatively, $R^1$, $R^2$, $R^3$ and $R^4$ may be lower-alkylene groups which are bonded to each other to form a ring or rings. The lower-alkylene groups include, for example, methylene, ethylene, propylene and butylene. These $R^1$, $R^2$, $R^3$, $R^4$ and $R^5$ may all be the same, may partially be the same or may all be different groups.

One of the starting material represented by formula (I) may be prepared in high yield by reacting 2-dichloromethyl-3-chloro-2-propenenitrile, which is an product obtainable by the high temperature vapor phase chlorination of methacrylonitrile, with an alcohol in the presence of a sodium alcoholate [see Yakugaku Zasshi, 1294, 93 (1973) and ibid., 1285, 93 (1973)].

The 2-alkoxymethylene-3,3-dialkoxypropanenitrile (II) compounds are novel and may be obtained by, for example, reacting a 3-alkoxy-2-propenenitrile or a 3,3-dialkoxypropanenitrile with a formylating agent such as a formic acid ester and carbon monoxide in the presence of an alkali metal alcoholate at a temperature of 0° to 100° C. to obtain an alkali metal salt of a 2-hydroxymethylene-3,3-dialkoxypropanenitrile and then reacting the thus obtained salt with an alkylating agent such as a dialkylsulfuric acid and an alkyl halide or with a mineral acid in an amount of not less than an equivalent for neutralization in an alcohol.

A particularly preferred process for preparing the 2-alkoxymethylene-3,3-dialkoxypropanenitrile of formula (II) is a novel process which comprises reacting an alkali metal salt of a 2-hydroxymethylene-3,3-dialkoxypropanenitrile with an alcohol which boils azeotropically with water, in the presence of an acid, while removing said alcohol and produced water from the reaction system by azeotropic distillation.

According to the novel process which has been invented by the present inventors, the desired 2-alkoxymethylene-3,3-dialkoxypropanenitrile (II) can be prepared in an extremely high yield of around 90%.

Next, the novel process for preparing the 2-alkoxymethylene-3,3-dialkoxypropanenitrile (II) will be described in detail.

The alkali metal salt of the 2-hydroxymethylene-3,3-dialkoxypropanenitrile, which is the starting material for the synthesis of 2-alkoxymethylene-3,3-dialkoxyepropanenitrile (II), can be represented by the following general formula (V).

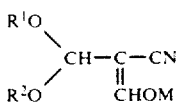

$$\begin{matrix} R^1O \\ \phantom{R^1O}\diagdown \\ \phantom{R^1O}\phantom{\diagdown}CH-C-CN \\ \phantom{R^1O}\diagup \phantom{CH-}\| \\ R^2O \phantom{\diagup}\phantom{CH-}CHOM \end{matrix} \qquad (V)$$

In the formula, R¹ and R² have the same meanings as defined above and M may include an alkali metal such as sodium, potassium, lithium and rubidium.

As the acid to be used in the process for preparing the compound of formula (II), there may be mentioned such an inorganic acid as concentrated sulfuric acid, concentrated hydrochloric acid, hydrogen chloride, and concentrated phosphoric acid, and such an organic acid as p-toluenesulfonic acid and acetic acid.

These acids are used in an amount of not less than an equivalent for neutralization, typically 1 to 10 equivalents, preferably 1 to 5 equivalents against the alkali metal salt of the 2-hydroxymethylene-3,3-dialkoxypropanenitrile.

As the representative examples of the alcohol which evaporates azeotropically with water, there may be mentioned ethanol, propanols, butanols, pentanols, and the like. The most preferred alcohol is n-butanol. These alcohols may be employed typically in an amount of 3 to 200 parts by weight, preferably in an amount of 5 to 100 parts by weight per one part by weight of the alkali metal salt of the 2-hydroxymethylene-3,3-dialkoxypropanenitrile, since the progress of the reaction becomes insufficient when the amount to be used thereof is too small and thus the yield of the desired product is decreased, and since the use of larger amount thereof is less economical although any excess amount thereof does not affect badly the reaction.

The reaction is carried out under ambient or reduced pressure at a temperature of 0° to 120° C. for 1 to 10 hours while removing the formed water from the reaction system by azeotropic distillation with the used lower-alcohol. In cases where the reaction is not conducted while removing the water from the reaction system, the yield of the desired product becomes extremely low.

In the process for preparing the compound of formula (II) any solvent is not necessarily needed. However, the azeotropic evaporation of the water formed by the reaction may be promoted by using a solvent inert to the reaction which forms an azeotropic mixture of a ternary system with water and the lower-alcohol. As such solvents, there may be mentioned hydrocarbon group solvents such as benzene, toluene, hexane, heptane and cyclohexane; and halogenated hydrocarbon group solvents such as carbon tetrachloride, methylene chloride, ethylene dichloride, trichloroethylene and tetrachloroethylene.

The thus formed products, 2-alkoxymethylene-3,3-dialkoxypropanenitriles (II) may be reacted as such, without isolation thereof, with amidines in the next step to obtain desired end products.

The products, 2-alkoxymethylene-3,3-dialkoxypropanenitriles (II) may readily be isolated and purified by optionally adopting a procedure or procedures such as filtration, neutralization, extraction, distillation and so forth. The thus isolated products may also be used as the starting material for obtaining the final desired product.

The starting material of formula (I) may also be obtained easily by subjecting a 2-alkoxymethylene-3,3-dialkoxypropanenitrile (II) to reaction with a corresponding aliphatic alcohol in the presence of an alkali metal alcoholate corresponding to the alkoxyl group to be introduced at a temperature of 0° to 150° C. for 0.1 to 24 hours.

As the alcohol to be used, there may be mentioned methanol, ethanol, propanol, butanol and the like.

The amount of the alcohol to be used is in the range of 10 to 500 moles per one mole of the 2-alkoxymethylene-3,3-dialkoxypropanenitrile (II).

As the alkali metal to be used for the alcoholate, there may be mentioned sodium, potassium and so on. The amount of the alcoholate to be used is in the range of 0.05 to 5 moles per one mole of the starting compound (II). Further, the above-mentioned reaction may be carried out in an inert solvent, for example, an ether group solvent, such as tetrahydrofuran, dioxane, dimethoxyethane, diethyl ether and diisopropyl ether, and a hydrocarbon group solvent such as benzene, toluene, xylene, hexane and heptane.

The isolation of the thus formed compound (II) may readily be carried out by optionally adopting such a procedure as neutralization, filtration, extraction, concentration, distillation and so on.

In the present invention, the above-mentioned starting propanenitriles represented by the above general formula (I) or (II) may either be employed alone or may be used in the state of a mixture.

Further, as the amidine represented by the above general formula (III) which is the other starting material, there may be mentioned, for example, formamidine, acetamidine, propioamidine, butanoamidine, pentanoamidine, benzamidine, toluamidine, ethylbenzamidine, propylbenzamidine, methoxybenzamidine, ethoxybenzamidine, chlorobenzamidine, bromobenzamidine and the like. Since these amidines are unstable compounds, it is preferred to use them in the form of a salt with an inorganic acid such as hydrochloric acid, sulfuric acid and nitric acid or with an organic acid such as acetic acid and to obtain a free amidine in the reaction system. As the useful base to be used for obtaining a free amidine in the reaction system, there may be mentioned a sodium alcoholate, an alkali hydroxide, an alkali carbonate, an alkali bicarbonate, a strongly basic ion exchange resin and so on. The amidine salt may be used in an amount of 0.5 to 10 moles, preferably 1 to 5 moles per one mole of the propanenitrile represented by the above general formula (I) or (II). The abovementioned base is employed in an amount of around an equivalent for neutralization.

The reaction may be carried out without any solvent or may be carried out in a solvent which is inert to the reaction. As such solvents, an aliphatic alcohol such as methanol, ethanol, propanol and butanol is most preferable. However, ether group solvents such as dioxane, tetrahydrofuran, dimethoxyethane, diethyl ether, diisopropyl ether and dibutyl ether; aromatic hydrocarbon group solvents such as benzene, toluene and xylene; halogenated hydrocarbon g.oup solvents such as methylene chloride, chloroform, carbon tetrachloride and 1,2-dichloroethane, nitrile group solvents such as acetonitrile, propionitrile and benzonitrile; and so on may also be used for the reaction. These solvents may preferably be employed in an amount of 0.5 to 20 parts by weight per one part by weight of the compound represented by the general formula (I) or (II) (in case of a mixture, per one part of the total amount thereof).

The reaction is carried out at a temperature of 0° to 150° C. under ambient pressure or under positive pressure for 0.1 to 24 hours. The reaction may be carried out either by a batch system or by a continuous system. The isolation of the desired product from the reaction mixture may readily be conducted by optionally adopting a procedure such as filtration, concentration, extraction, recrystallization and so forth.

According to the process of this invention, the 4-amino-5-dialkoxymethylpyrimidine derivative represented by the above general formula (IV) can be prepared in a more simplified method as compared with the processes known to the art.

The 4-amino-5-dialkoxymethylpyrimidine derivative represented by the above general formula (IV) obtained by the process of this invention may readily be converted into a 4-amino-5-aminomethylpyrimidine derivative, which is an important compound as an intermediate for the synthesis of Vitamin-$B_1$, by, for example, hydrolysis thereof in the presence of an acid followed by reductive amination of the thus obtained 4-amino-5-formylpyrimidine derivative.

Next, Examples and Synthesis examples will be illustrated below.

EXAMPLE 1

In a 300 ml four-necked flask equipped with a stirrer, a dropping funnel, a thermometer and a condenser arranged downwardly, there were introduced 8.25 g (50 mmoles) of sodium salt of 2-hydroxymethylene-3,3-dimethoxypropanenitrile and 160 g of n-butanol. Then, with stirring the mixture at room temperature, 3.06 g (30 mmoles) of conc. sulfuric acid was gradually added dropwise thereto. After stirring for one hour, the mixture was heated under a reduced pressure of 23 to 25 mmHg and the temperature of the liquid was maintained at 43° to 45° C. to distil out such lower-boiling fractions as alcohol and water. After 1.5 hours from the starting of the distilling out, 120 g of n-butanol was further added dropwise thereto, and the reaction was continued for further 2 hours while distilling out the lower-boiling fractions under the same temperature and the same pressure as in the above-mentioned conditions to obtain 170 g in total of a distillate.

After cooling, the reaction mixture was subjected to filtration to remove the insoluble inorganic salt. Thereafter, the filtrate was concentrated followed by distillation under reduced pressure to remove the low-boiling fraction to obtain 12.7 g (yield: 90%) of a colorless oil boiling at 153° to 156° C./0.5 mmHg.

The thus obtained product was confirmed to be 2-n-butoxymethylene-3,3-di-n-butoxypropanenitrile from the analyses by NMR, IR and MS.

EXAMPLE 2

Into the same apparatus as in Example 1, were introduced 8.25 g (50 mmoles) of sodium salt of 2-hydroxymethylene-3,3-dimethoxypropanenitrile and 120 g of n-butanol. With stirring the mixture at room temperature, 80 g (hydrogen chloride 100 mmoles) of a 4.6 wt. % solution of hydrogen chloride in n-butanol was gradually added. After stirring for one hour, the mixture was heated under a reduced pressure of 23 to 25 mmHg and the temperature of the liquid was maintained at 43° to 45° C. to distil out such a low-boiling fraction as alcohol and water. After starting the distilling out, the reaction was continued for 2 hours to obtain 130 g of a distillate.

After cooling, the reaction mixture was subjected to gas chromatographic analysis according to the internal standard method for quantitative determination. As a result, it was confirmed that 2-n-butoxymethylene-3,3-di-n-butoxypropanenitrile was prooduced in a yield of 92%.

EXAMPLE 3

Into the same apparatus as in Example 1, were introduced 7.47 g (30 mmoles) of sodium salt of 2-hydroxymethylene-3,3-di-n-butoxypropanenitrile and 40 g of n-butanol. With stirring at room temperature, 1.73 g (17 mmoles) of conc. sulfuric acid was gradually added thereto. After stirring for one hour, the mixture was heated under a reduced pressure of 33 to 35 mmHg and the temperature of the liquid was maintained at 50° to 52° C. to distil out such a low-boiling fraction as n-butanol and water. After starting of the distilling out, 160 g of n-butanol was added dropwise thereto over 3 hours while maintaining the temperature and pressure at the same level as in the above and the reaction was continued further for 0.5 hours to obtain 160 g in total of a distillate.

After cooling, the reaction mixture was subjected to quantitative analysis in the same manner as in Example 2. As a result, it was confirmed that 2-n-butoxymethylene-3,3-di-n-butoxypropanenitrile was produced in a yield of 93%.

EXAMPLE 4

Into the same apparatus as in Example 1, were introduced 3.86 g (20 mmoles) of sodium salt of 2-hydroxymethylene-3,3-diethoxypropanenitrile, 100 g of ethanol and 100 g of n-hexane. With stirring at room temperature, 1.22 g (12 mmoles) of conc. sulfuric acid was gradually added dropwise thereto. After stirring for one hour, the mixture was heated under ordinary pressure and such a low-boiling fraction as ethanol, n-hexane and water was distilled out at a distillation temperature of 56° to 58° C. After starting of the distilling out, a mixture of 250 g of ethanol and 900 g of n-hexane was added dropwise thereto over six hours while maintaining the distillation temperature at the same level and the reaction was further conducted for one hour to obtain 1250 g in total of a distillate.

Subsequently, the reaction mixture was treated in the same manner as in Example 1 to obtain 3.58 g (yield: 90%) of a colorless transparent oil boiling at 120° to 123° C./2 mmHg. The thus obtained product was confirmed to be 2-ethoxymethylene-3,3-diethoxypropanenitrile according to the analyses by NMR, IR and MS.

EXAMPLE 5

Into the same apparatus as in Example 1, were introduced 7.47 g (30 mmoles) of sodium salt of 2-hydroxymethylene-3,3-di-n-butoxypropanenitrile and 200 g of n-butanol. With stirring the mixture at room temperature, 1.73 g (17 mmoles) of conc. sulfuric acid was gradually added dropwise thereto. After stirring for one hour, the temperature of the liquid was maintained at 50° to 52° C. and the reaction was carried out for 3.5 hours.

After cooling, the reaction mixture was subjected to quantitative analysis in the same manner as in Example 2 to confirm that 2-n-butoxymethylene-3,3-di-n-butoxypropanenitrile was produced in a yield of 57%.

EXAMPLE 6

In a 300 ml autoclave made of stainless steel, there were placed 16.6 g (200 mmoles) of 3-methoxy-2-propenenitrile, 13.0 g (240 mmoles) of sodium methylate, 12.8 g (400 mmoles) of methanol and 65 ml of toluene. After the atmosphere of the reaction system was replaced by nitrogen, the mixture was heated up to around 40° C. under stirring and CO was pressured in the autoclave so that the pressure might be around 50 kg/cm$^2$G. The consumed CO was supplemented condinuously and the reaction was continued for 3 hours. After cooling of the reaction mixture, the gas in the autoclave was purged off and the reaction mixture was transferred completely to a 300 ml four-necked flask equipped with a calcium chloride tube, a stirrer, a dropping funnel and a thermometer. While maintaining the liquid temperature at around 20° C. or less, 30.3 g (240 mmoles) of dimethylsulfuric acid was added dropwise thereto over 30 minutes with stirring the contents in the flask, and the reaction was carried out at around 50° C. for about 4 hours.

After the reaction mixture was cooled and the insoluble substance was removed by filtration, the collected insoluble were washed with toluene and the washing was combined with the filtrate followed by washing with a 50 wt. % aqueous sodium hydroxide and then with water. Subsequently, after drying over sodium sulfate, the toluene layer was evaporated under reduced pressure to remove low-boiling fractions and to obtain 17.6 g (yield: 56%) of a colorless transparent oil boiling at 104°-106° C./2 mmHg.

The thus obtained product was confirmed to be 2-methoxymethylene-3,3-dimethoxypropanenitrile according to analyses by NMR, IR and MS.

EXAMPLE 7

In a mixed solvent of 100 ml of toluene and 50 ml of methanol was dissolved 7.85 g (50 mmoles) of 2-methoxymethylene-3,3-dimethoxypropanenitrile. To the resulting solution was added 9.65 g (50 mmoles) of a 28 wt. % solution of sodium methylate in methanol and the mixture was stirred at room temperature for one and a half hours. Subsequently, the reaction mixture was concentrated under reduced pressure to remove the methanol by distillation. To the resulting residue was added 25 ml of water and the toluene layer was separated followed by drying over anhydrous sodium sulfate. The thus dried toluene solution was distilled to obtain 8.50 g (45 mmoles) of 2-dimethoxymethyl-3,3-dimethoxypropanenitrile as a colorless transparent oil boiling at 90°-93° C./2 mmHg.

EXAMPLE 8

In 100 ml of n-butanol was dissolved 8.49 g (30 mmoles) of 2-n-butoxymethylene-3,3-di-n-butoxypropanenitrile. To the resulting solution was added 0.87 g (9 mmoles) of sodium n-butylate at room temperature, and the mixture was stirred at room temperature for one hour. Then, the reaction mixture was neutralized with a solution of sulfuric acid in butanol and the resulting inorganic salt was removed by filtration. The filtrate was distilled under reduced pressure to obtain 9.10 g (25 mmoles) of 2-di-n-butoxymethyl-3,3-di-n-butoxypropanenitrile as a colorless transparent oil boiling at 170°-175° C./2 mmHg.

In the following Examples, the starting materials have been obtained by one of the processes as described above in Examples 1 to 8.

EXAMPLE 9

In a 50 ml four-necked flask equipped with a calcium-chloride tube, a thermometer and a reflux condenser, there were placed 11.6 g (60 mmoles) of a 28 wt. % solution of sodium methylate in methanol and 10 ml of methanol. Thereto was added with stirring 5.67 g of acetamidine hydrochloride (60 mmoles) and the mixture was stirred at room temperature for 30 minutes. Then, 7.85 g (50 mmoles) of 2-methoxymethylene-3,3-dimethoxypropanenitrile was added thereto and the mixture was heated and refluxed for 5 hours. After completion of the reaction, the reaction mixture was cooled and then the insoluble sodium chloride was removed by filtration. After concentration of the solvent, methanol, 50 ml of water was added thereto and the mixture was extracted four times with 20 ml of methylene chloride. After the extract was dried over sodium sulfate, the sodium sulfate was removed by filtration and the filtrate was concentrated to dryness to obtain a white crude crystal. The thus obtained product was recrystallized from a mixed solvent of 50 ml of hexane and 25 ml of toluene to obtain 8.05 g (yield: 88%) of 2-methyl-4-amino-5-dimethoxymethylpyrimidine melting at 102°-104° C.

EXAMPLE 10

In the same reaction apparatus as in Example 9, there was placed 11.6 g (60 mmoles) of a 28 wt. % solution of sodium methylate in methanol. Thereto was added with stirring 5.67 g (60 mmoles) of acetamidine hydrochloride, and the mixture was stirred at room temperature for one hour. Subsequently, 9.45 g (50 mmoles) of 2-dimethoxymethyl-3,3-dimethoxypropanenitrile was added thereto and the mixture was heated and refluxed for 5 hours. After completion of the reaction, the reaction mixture was cooled and the insoluble sodium chloride was removed by filtration. The filtrate was analyzed by gas chromatography according to the internal standard method. As the result, it was confirmed that 8.51 g (yield: 93%) of 2-methyl-4-amino-5-dimethoxymethylpyrimidine had been formed.

EXAMPLE 11

An experiment was carried out in the same manner as in Example 10 except that a mixture containing 3.31 g of 2-dimethoxymethyl-3,3-dimethoxypropanenitrile (17.5 mmoles) and 5.10 g (32.5 mmoles) of 2-methoxymethylene-3,3-di-methoxypropanenitrile was used in place of the 2-dimethoxymethyl-3,3-dimethoxypropanenitrile. The yield of 2-methyl-4-amino-5-dimethoxymethylpyrimidine was 91%.

EXAMPLE 12

In the same apparatus as in Example 9, there were placed 2.84 g (30 mmoles) of acetamidine hydrochloride and 15 ml of ethanol. Thereto was added with stirring 2.04 g (30 mmoles) of sodium ethylate and the mixture was stirred at room temperature for 30 minutes. Subsequently, a mixture containing 2.45 g (10 mmoles) of 2-diethoxymethyl-3,3-diethoxypropanenitrile and 2.99 g (15 mmoles) of 2-ethoxymethylene-3,3-diethoxypropanenitrile was added thereto and the mixture was heated followed by reflux for 4 hours. After cooling, sodium chloride was removed and the filtrate was subjected to gas chromatographic analysis. The yield of 2-methyl-4-amino-5-diethoxymethylpyrimidine was 88%.

EXAMPLE 13

In the same apparatus as in Example 9, 2.84 g (30 mmoles) of acetoamidine hydrochloride was added to an n-butanolic solution of sodium butylate which had been prepared with 0.69 g (30 mg atoms) of sodium and 15 ml of butanol, and the mixture was stirred at room temperature for 30 minutes. Then, 7.08 g (25 mmoles) of 2-n-butoxymethylene-3,3-di-n-butoxypropanenitrile was added thereto and the mixture was heated. Thereafter, the resulting mixture was stirred under heating at about 90° C. for 5 hours. After cooling, the sodium chloride was removed and the remaining liquid was subjected to gas chromatographic analysis for quantitative determination. The yield of 2-methyl-4-amino-5-di-n-butoxymethylpyrinidine was 85%.

EXAMPLE 14

An experiment was conducted in the same manner as in Example 9 except that 9.40 g (60 mmoles) of benzamidine hydrochloride was used in place of the acetamidine hydrochloride to obtain white crude crystals. These crystals thus obtained were recrystallized from a mixed solvent of hexane and toluene (volume ratio 2:1) to obtain 10.4 g (yield: 85%) of 2-phenyl-4-amino-5-dimethoxymethyl-pyrimidine melting at 116°-118° C.

EXAMPLE 15

An experiment was carried out in the same manner as in Example 10 except that 7.75 g (50 mmoles) of methoxymethylenecyanoacetaldehyde ethylene acetal was used in place of 2-dimethoxymethyl-3,3-dimethoxypropanenitrile.

The yield of ethylene acetal of 2-methyl-4-amino-5-formylpyrimidine was 83%.

EXAMPLE 16

An experiment was conducted in the same manner as in Example 10 except that 4.83 g (60 mmoles) of formamidine hydrochloride was used in place of acetamidine hydrochloride. The yield of 4-amino-5-dimethoxymethylpyrimidine was 90%.

EXAMPLE 17

An experiment was conducted in the same manner as in Example 10 except that 6.51 g (60 mmoles) of propioamidine hydrochloride was used in place of acetamidine hydrochloride.

The yield of 2-ethyl-4-amino-5-dimethoxymethylpyrimidine was 89%.

EXAMPLE 18

In a 200 ml four-necked flask equipped with a stirrer, a dropping funnel, a thermometer and a condenser arranged downwardly, there were introduced 8.25 g (50 mmoles) of sodium salt of 2-hydroxymethylene-3,3-dimethoxypropanenitrile and 60 g of n-butanol. To the mixture was gradually added dropwise, with stirring, 2.76 g (27 mmoles) of conc. sulfuric acid. After stirring for one hour, the temperature of the mixture was raised under a reduced pressure of 33-35 mmHg, and then was maintained at 50° to 52° C. to distil out such a low-boiling fraction as an alcohol and water. After starting of the distillation, 160 g of n-butanol was added dropwise thereto over 2 hours while maintaining the temperature and the pressure at the same level, and the reaction was further continued for 30 minutes to obtain 160 g in total of a distillate when the heating was stopped and the reaction system was returned to an ordinary pressure. Subsequently, the downwardly arranged condenser was replaced with a reflux condenser equipped with a calcium chloride tube. Then, a mixture of 5.20 g (55 mmoles) of acetamidine hydrochloride and 30.0 g (62.5 mmoles) of a 20 wt. % solution of sodium n-butylate in n-butanol, which had been stirred under reduced pressure in a dry atmosphere for 30 minutes, was gradually added dropwise, with stirring, to the flask from the dropping funnel.

Thereafter, the temperature of the mixture was raised and the resulting mixture was stirred under heating at 85° to 90° C. for around 4 hours.

After cooling, sodium chloride was removed by filtration and the filtrate thus obtained was subjected to quantitative analysis by gas chromatography. As the result, it was found that 11.0 g (41.2 mmoles) of 2-methyl-4-amino-5-di-n-butoxymethylpyrimidine was obtained. The yield of the product is 82% based on the starting material, i.e., sodium salt of 2-hydroxymethylene-3,3-dimethoxypropanenitrile.

We claim:

1. A process for preparing a 4-amino-5-dialkoxymethylpyrimidine compound represented by the formula

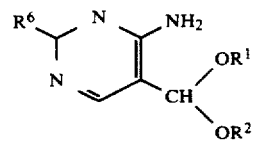

wherein $R^1$ and $R^2$ may be the same or different and each represent a lower-alkyl group having 1-4 carbon atoms or $R^1$ and $R^2$ may be lower-alkylene groups having 1-4 carbon atoms which are bonded to each other to form a a ring; and $R^6$ represents a hydrogen atom, a lower-alkyl group having 1-4 carbon atoms or a phenyl group wherein the hydrogen atom or atoms may be replaced by a lower-alkyl group having 1-3 carbon atoms, a lower-alkoxy group having 1 or 2 carbon atoms or a halogen atom, which comprises reacting a propanenitrile compound represented by formula (I) or (II)

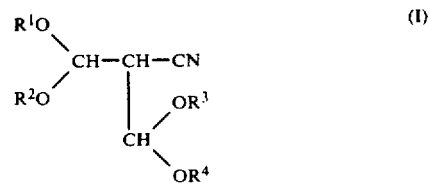

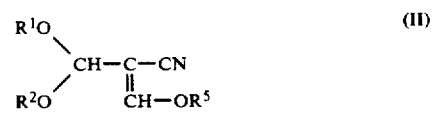

wherein $R^1$, $R^2$, $R^3$, $R^4$ and $R^5$ may be the same or different and each represent a lower-alkyl group having 1-4 carbon atoms or $R^1$, $R^2$, $R^3$ and $R^4$ may be lower-alkylene groups having 1-4 carbon atoms which are bonded to each other to form at least one ring, with an amidine represented by the formula

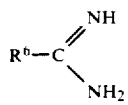

wherein $R^6$ has the same meaning as defined above.

2. The process of Claim 1, wherein $R^1$, $R^2$, $R^3$, $R^4$, $R^5$ and $R^6$ are each selected from the group consisting of methyl, ethyl, propyl and butyl.

3. The process of claim 1, wherein the amidine is selected from the group consisting of formamidine, acetamidine, propioamidine, butanoamidine, pentanoamidine, benzamidine, toluamidine, ethylbenzamidine, propylbenzamidine, methoxybenzamidine, ethoxybenzamidine, chlorobenzamidine and bromobenzamidine.

4. The process of claim 1, wherein the amidine is in the form of a salt of an inorganic or organic acid, said process further comprising converting said amidine salt into the free form of said amidine.

5. The process of claim 1, wherein the amidine is used in an amount of 0.5 to 10 moles per one mole of the propanenitrile represented by formula (I) or (II).

6. The process of claim 5, wherein the amidine is used in an amount of 1 to 5 moles per one mole of the propanenitrile represented by formula (I) or (II).

7. The process of claim 1, wherein the reaction is carried out at a temperature of 0° to 150° C. under ambient or positive pressure for 0.1 to 24 hours.

8. The process of claim 1, wherein the reaction is carried out in an inert solvent.

9. The process of claim 8, wherein the amount of the solvent is in the range of 0.5 to 20 parts by weight per one part by weight of the compound represented by formula (I) or (II).

10. The process of claim 1, wherein the propanenitrile represented by formula (II) is prepared by reacting an alkali metal salt of a 2-hydroxymethylene-3,3-dialkoxypropanenitrile with an alcohol which boils azeotropically with water, in the presence of an acid, while removing said alcohol and resulting water from the reaction system by azeotropic distillation.

11. The process of claim 10, wherein the alkali metal is selected from the group consisting of sodium, potassium, lithium and rubidium.

12. The process of claim 10, wherein the acid is selected from the group consisting of concentrated sulfuric acid, concentrated hydrochloric acid, hydrogen chloride, concentrated phosphoric acid, p-toluene-sulfonic acid and acetic acid.

13. The process of claim 10, wherein the amount of the acid is in the range of 1 to 10 equivalents based on the alkali metal salt of the 2-hydroxymethylene-3,3-dialkoxypropanenitrile.

14. The process of claim 13, wherein the amount of the acid is in the range of 1 to 5 equivalents based on the alkali metal salt of the 2-hydroxymethylene-3,3-dialkoxypropanenitrile.

15. The process of claim 10, wherein the alcohol is selected from the group consisting of ethanol, propanol, butanol and pentanol.

16. The process of claim 10, wherein the amount of the alcohol is in the range of 3 to 200 parts by weight per one part by weight of the alkali metal salt of the 2-hydroxymethylene-3,3-dialkoxypropanenitrile.

17. The process of claim 16, wherein the amount of the alcohol is in the range of 5 to 100 parts by weight per one part by weight of the alkali metal salt of the 2-hydroxymethylene-3,3-dialkoxypropanenitrile.

18. The process of claim 10, wherein the reaction for forming the propanenitrile represented by formula (II) is carried out under ambient or reduced pressure at a temperature of 0° to 120° C. for 1 to 10 hours.

* * * * *